United States Patent [19]

Sherts et al.

[11] Patent Number: 5,792,149
[45] Date of Patent: Aug. 11, 1998

[54] CLAMP APPLICATOR

[75] Inventors: Charles R. Sherts, Southport; Richard Yagami, Ridgefield, both of Conn.

[73] Assignee: United States Surgical Corporation, Norwalk, Conn.

[21] Appl. No.: 725,362

[22] Filed: Oct. 3, 1996

[51] Int. Cl.[6] ................................................. A61B 17/10
[52] U.S. Cl. .......................... 606/142; 606/139; 606/144; 606/151
[58] Field of Search .................... 606/139, 142, 606/143, 144, 151; 227/901, 902

[56] References Cited

U.S. PATENT DOCUMENTS

| | | |
|---|---|---|
| 3,506,012 | 4/1970 | Brown . |
| 3,518,993 | 7/1970 | Blake . |
| 3,877,434 | 4/1975 | Ferguson et al. . |
| 3,958,576 | 5/1976 | Komiya . |
| 4,038,987 | 8/1977 | Komiya . |
| 4,174,715 | 11/1979 | Hasson . |
| 4,192,315 | 3/1980 | Hilzinger et al. . |
| 4,241,734 | 12/1980 | Kandel et al. . |
| 4,269,190 | 5/1981 | Behney . |
| 4,274,415 | 6/1981 | Kanamoto et al. ............ 128/321 |
| 4,367,746 | 1/1983 | Derechinsky . |
| 4,374,523 | 2/1983 | Yoon . |
| 4,416,266 | 11/1983 | Baucom . |
| 4,444,187 | 4/1984 | Perlin . |
| 4,660,558 | 4/1987 | Kees, Jr. . |
| 4,671,282 | 6/1987 | Tretbar . |
| 4,681,107 | 7/1987 | Kees, Jr. . |
| 4,706,668 | 11/1987 | Backer . |
| 4,765,335 | 8/1988 | Schmidt et al. . |
| 4,777,949 | 10/1988 | Perlin . |
| 4,777,950 | 10/1988 | Kees, Jr. . |
| 4,796,625 | 1/1989 | Kees, Jr. . |
| 4,856,518 | 8/1989 | McFadden . |
| 4,932,955 | 6/1990 | Merz et al. . |
| 4,935,026 | 6/1990 | McFadden . |
| 4,943,298 | 7/1990 | Fujita et al. . |
| 4,961,743 | 10/1990 | Kees, Jr. et al. . |
| 4,966,603 | 10/1990 | Focelle et al. . |
| 4,971,055 | 11/1990 | von Zeppelin . |
| 5,026,379 | 6/1991 | Yoon . |
| 5,053,045 | 10/1991 | Schmidt et al. . |
| 5,059,202 | 10/1991 | Liang et al. . |
| 5,074,870 | 12/1991 | von Zeppelin . |
| 5,217,473 | 6/1993 | Yoon . |
| 5,242,456 | 9/1993 | Nash et al. . |
| 5,304,183 | 4/1994 | Gourlay et al. . |
| 5,312,426 | 5/1994 | Segawa et al. . |
| 5,368,600 | 11/1994 | Failla et al. . |
| 5,452,733 | 9/1995 | Sterman et al. . |
| 5,474,567 | 12/1995 | Stefanchik et al. . |
| 5,487,746 | 1/1996 | Yu et al. . |
| 5,514,148 | 5/1996 | Smith, III . |
| 5,520,701 | 5/1996 | Lerch . |
| 5,569,274 | 10/1996 | Rapacki et al. . |

FOREIGN PATENT DOCUMENTS

| | | |
|---|---|---|
| WO 93/09721 | 5/1993 | WIPO . |
| WO 93/18712 | 9/1993 | WIPO . |

*Primary Examiner*—Michael Buiz
*Assistant Examiner*—Tina T. D. Pham

[57] ABSTRACT

A clamp applicator is disclosed having a housing, a clamp support member extending distally from the housing, an actuator assembly and a locking device. The actuator assembly is movable with respect to the clamp support member into engagement with a clamp supported at the distal end of the clamp support member to bias the clamp to an open position. A locking device is provided to retain the actuator assembly in a position to maintain the clamp in the open position.

18 Claims, 17 Drawing Sheets

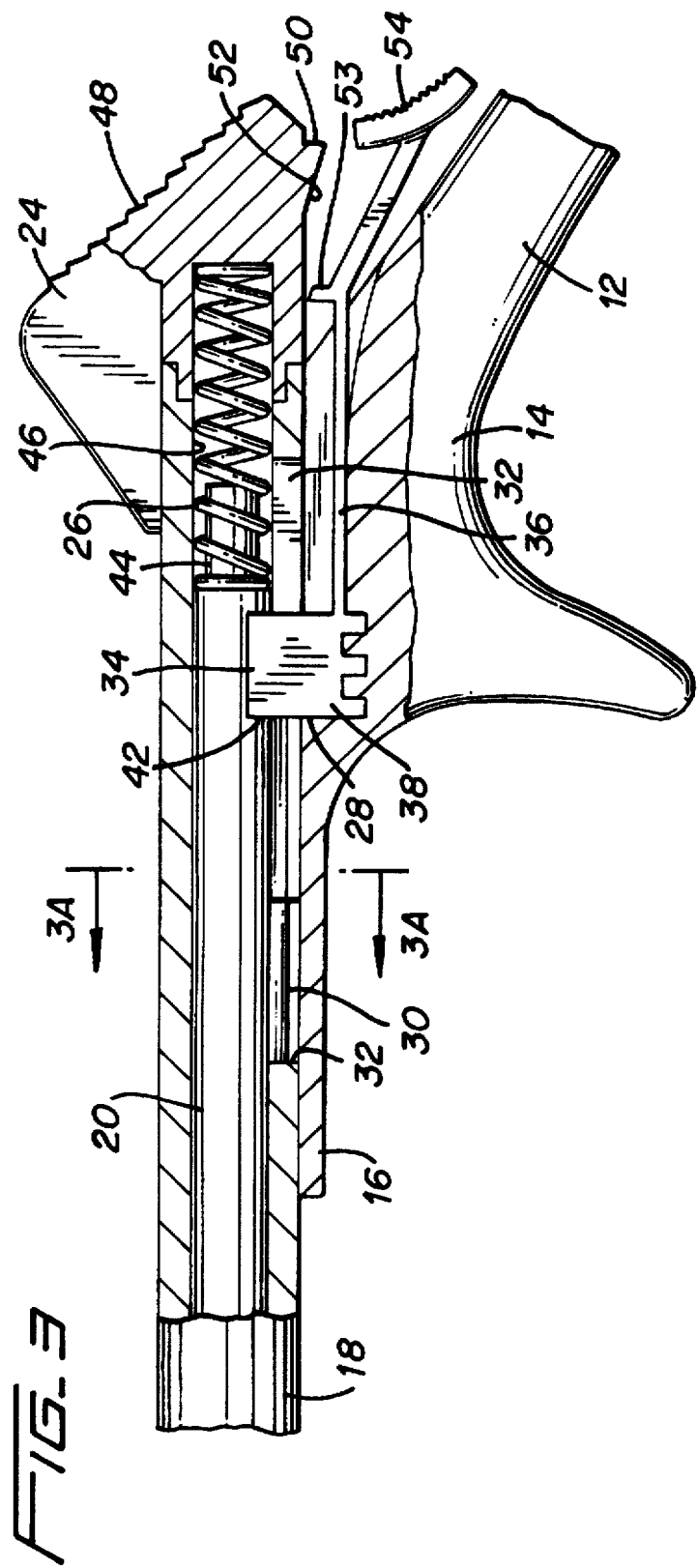
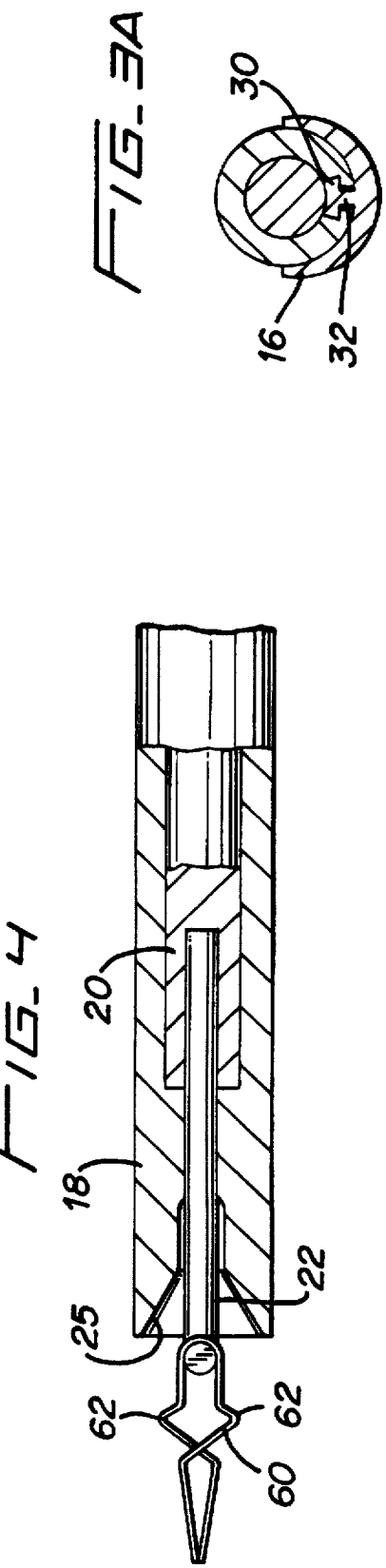

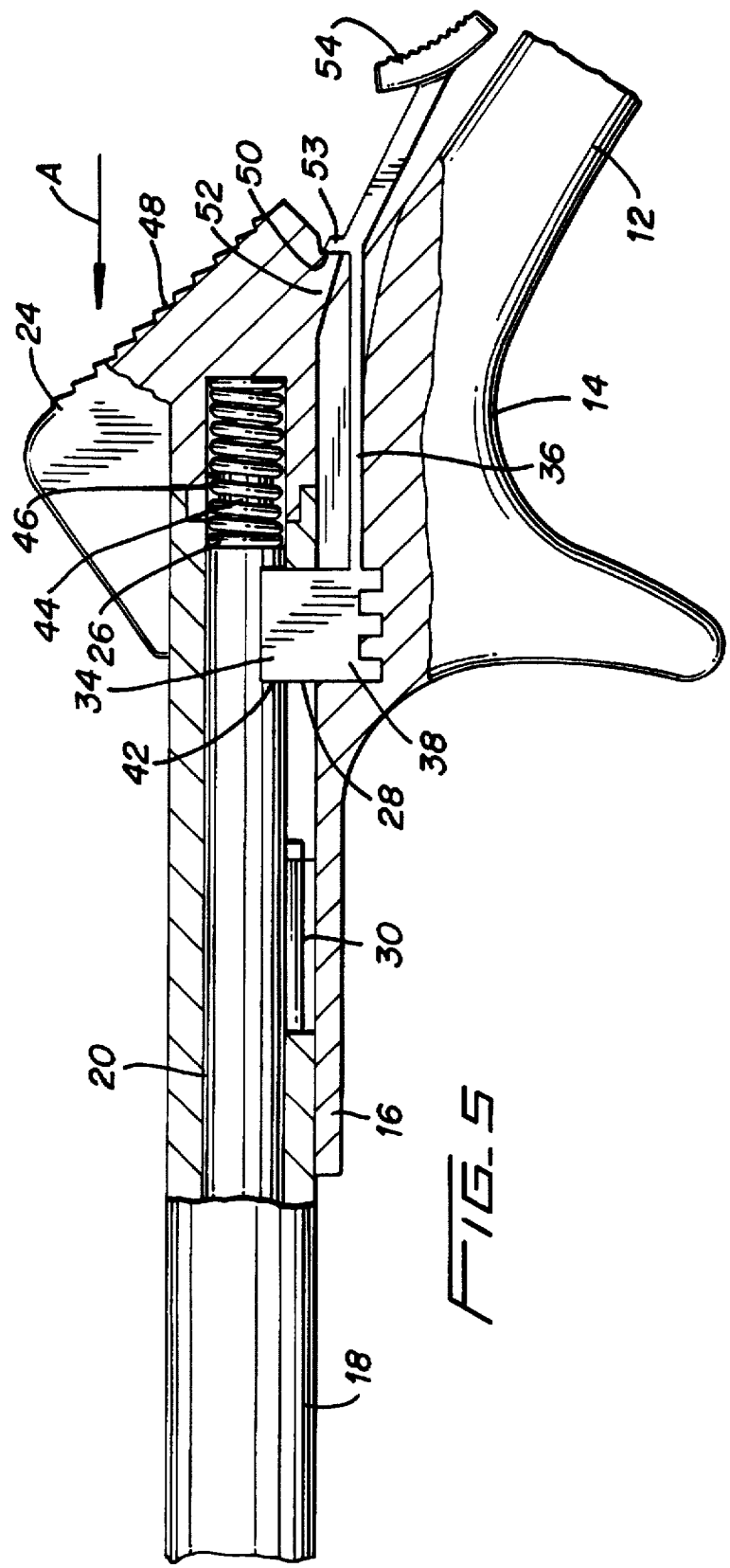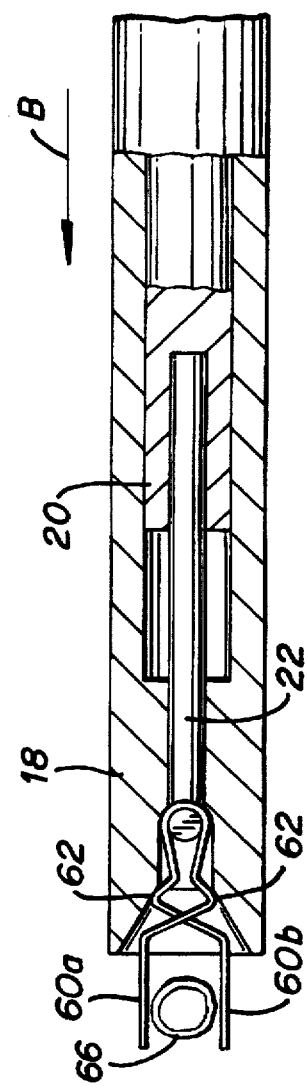

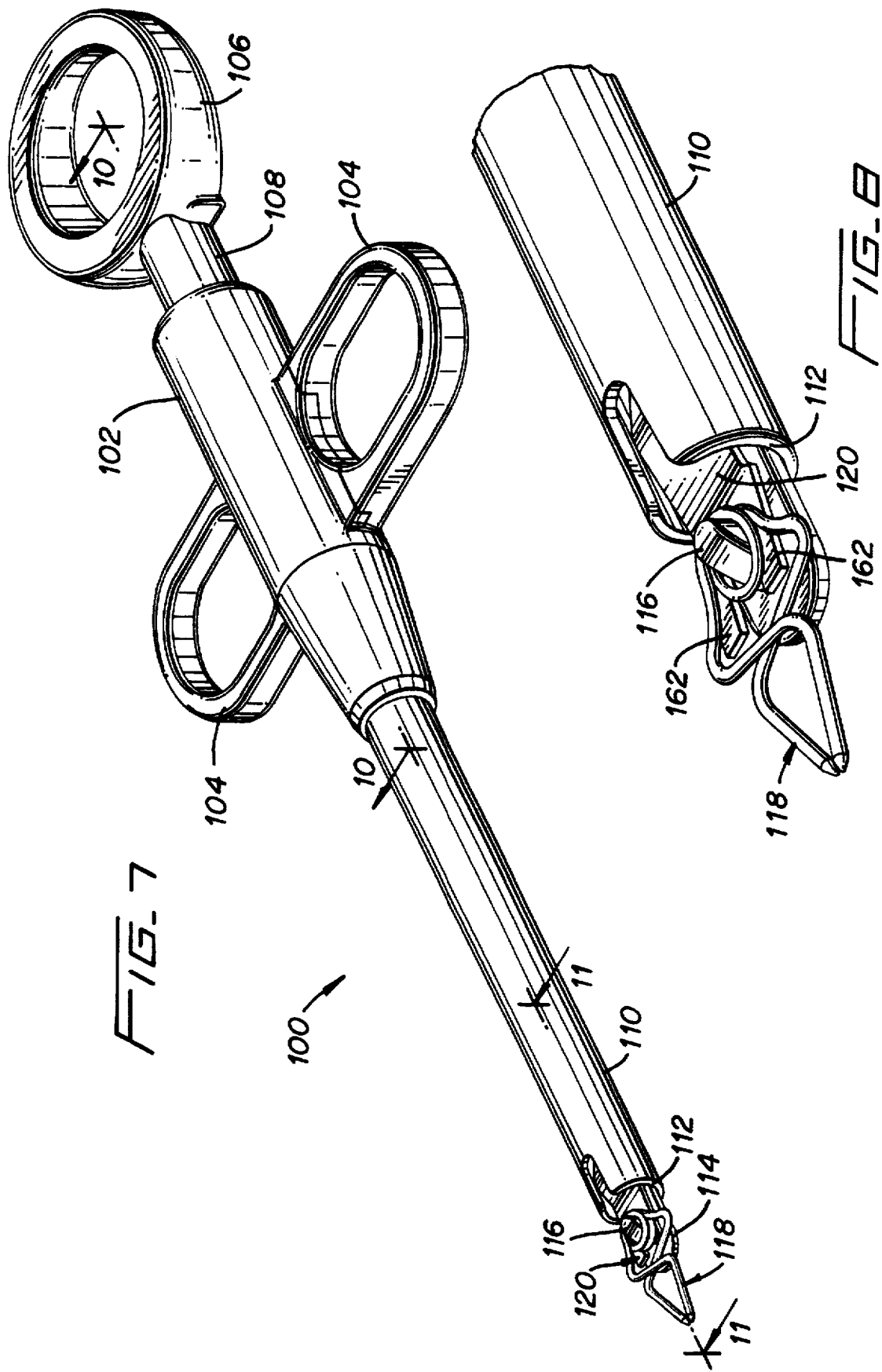

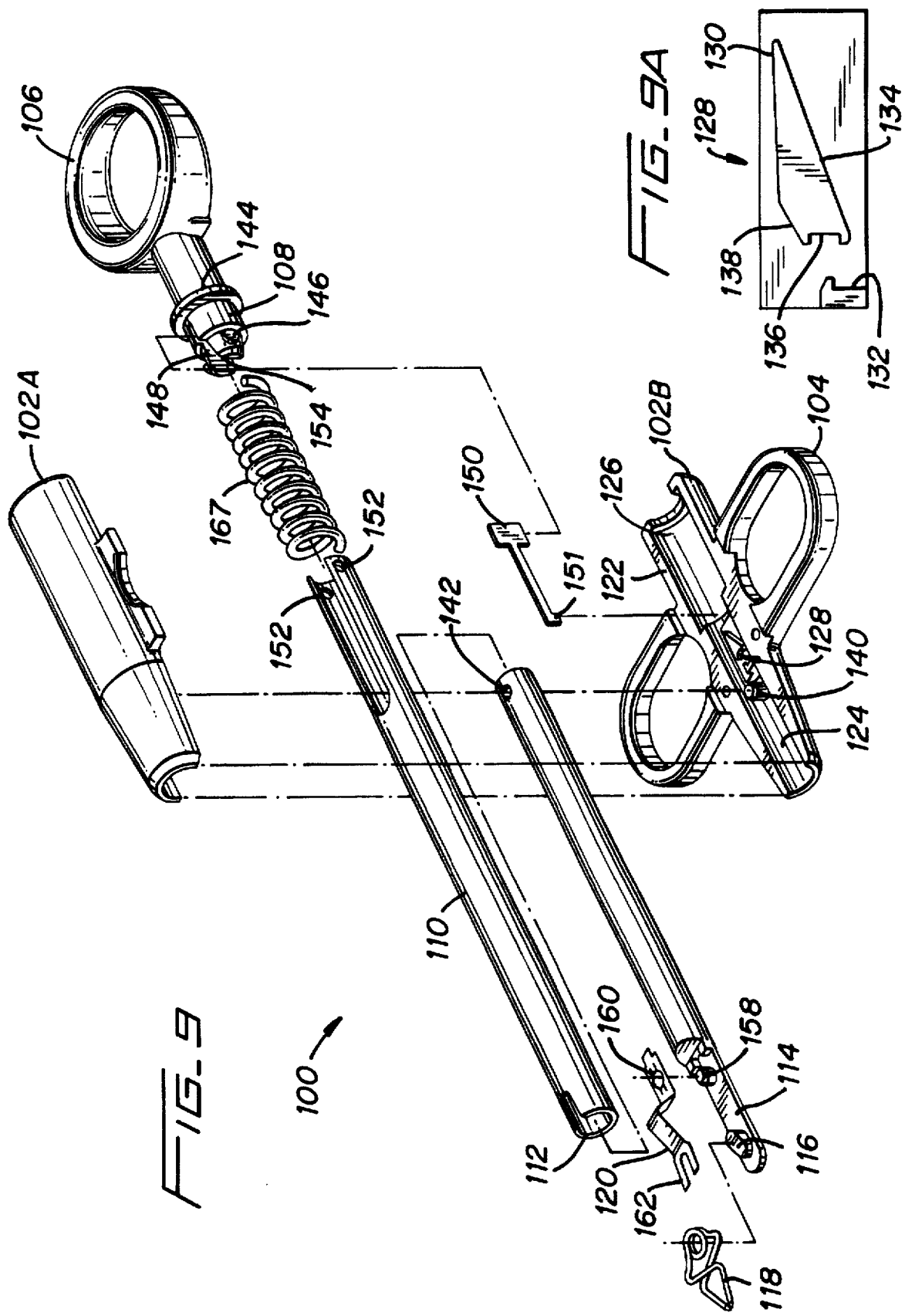

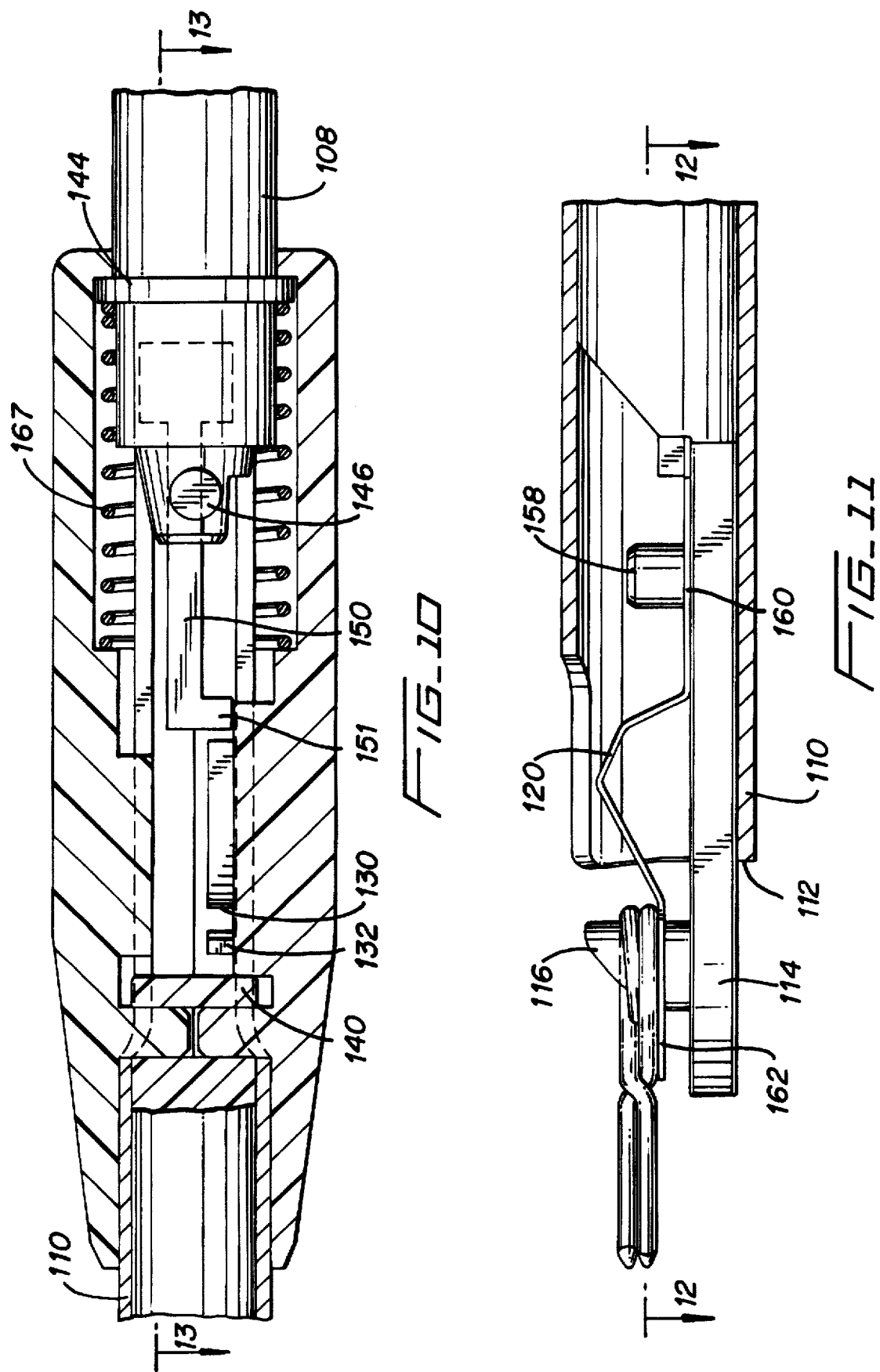

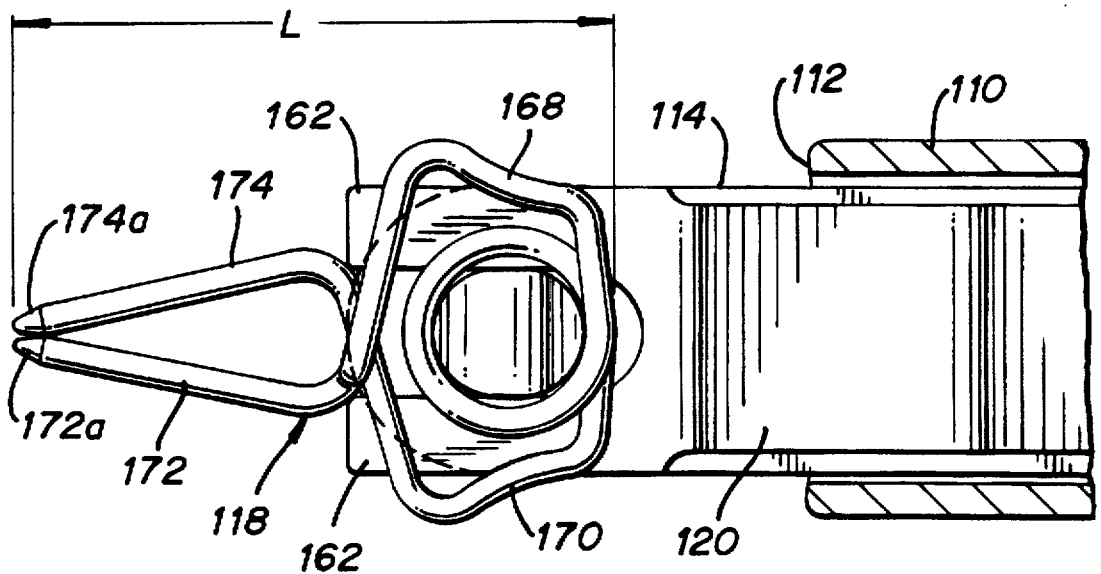
FIG_12
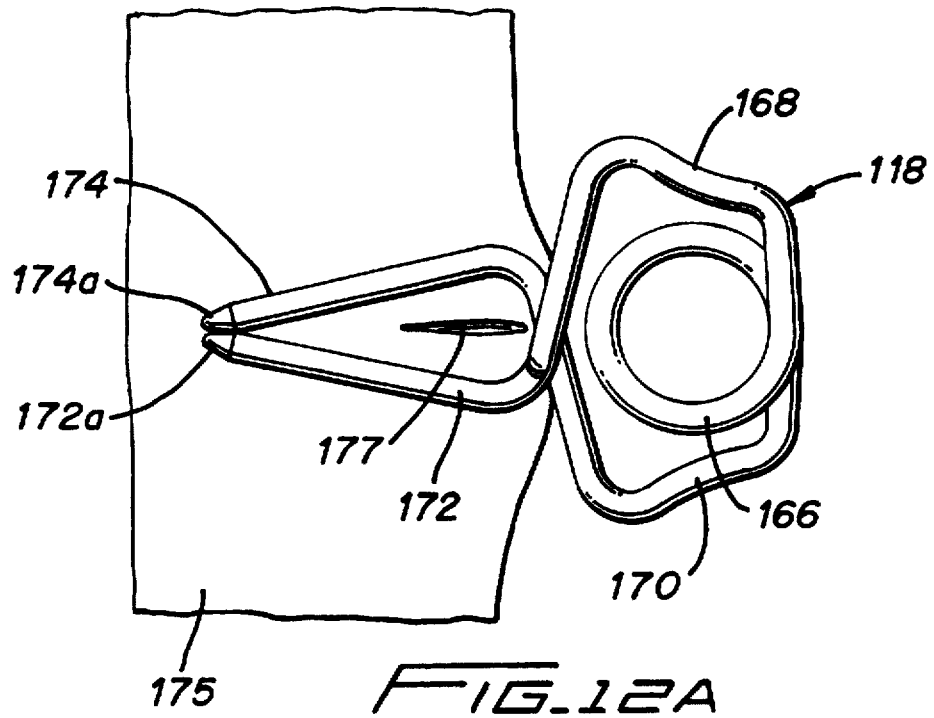
FIG_12A

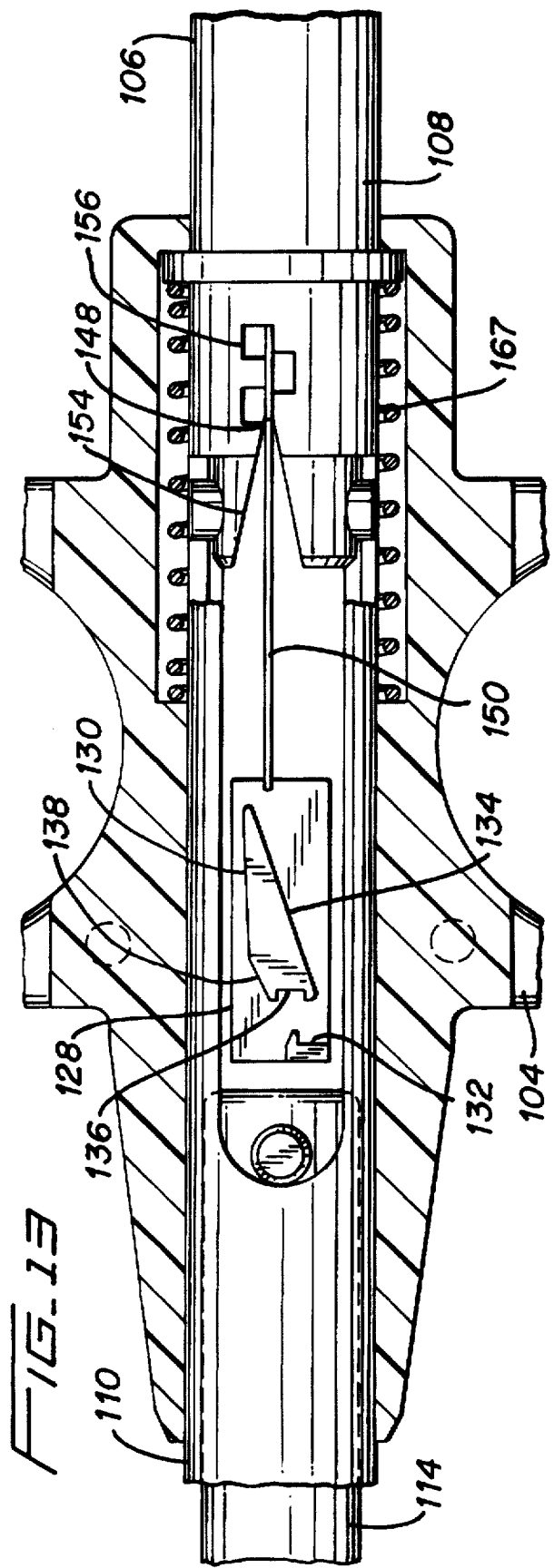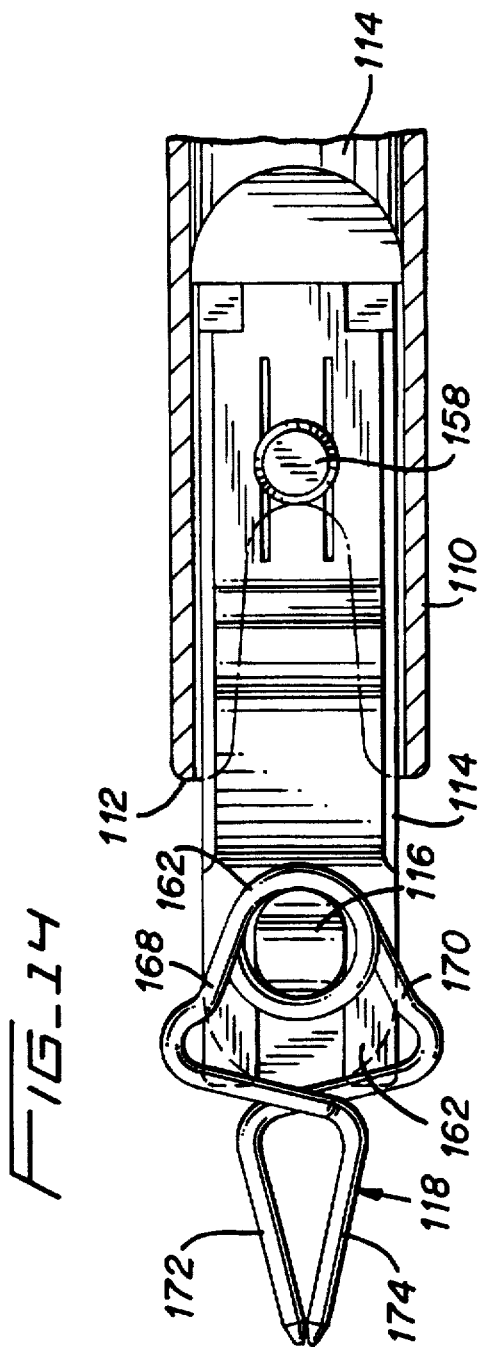

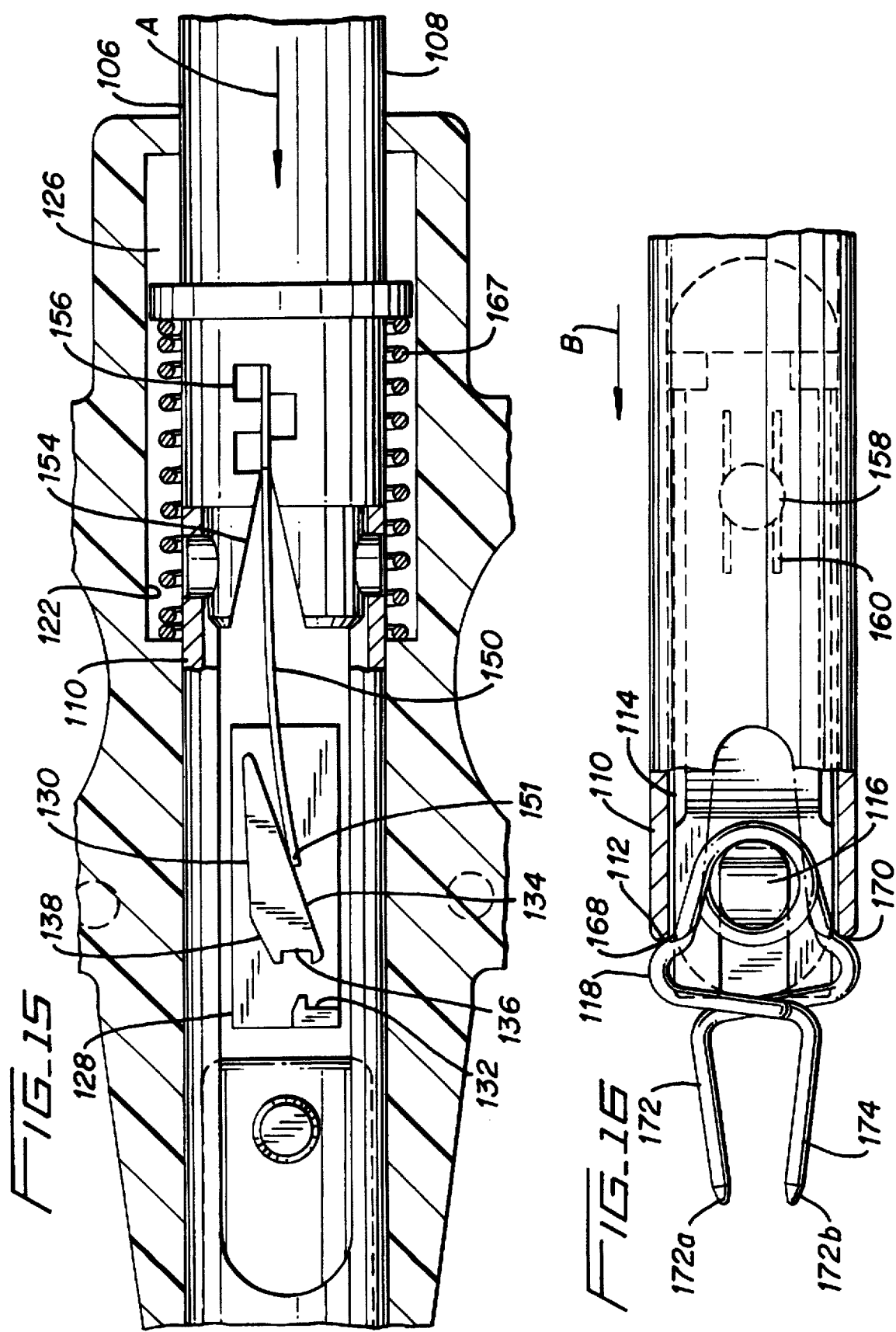

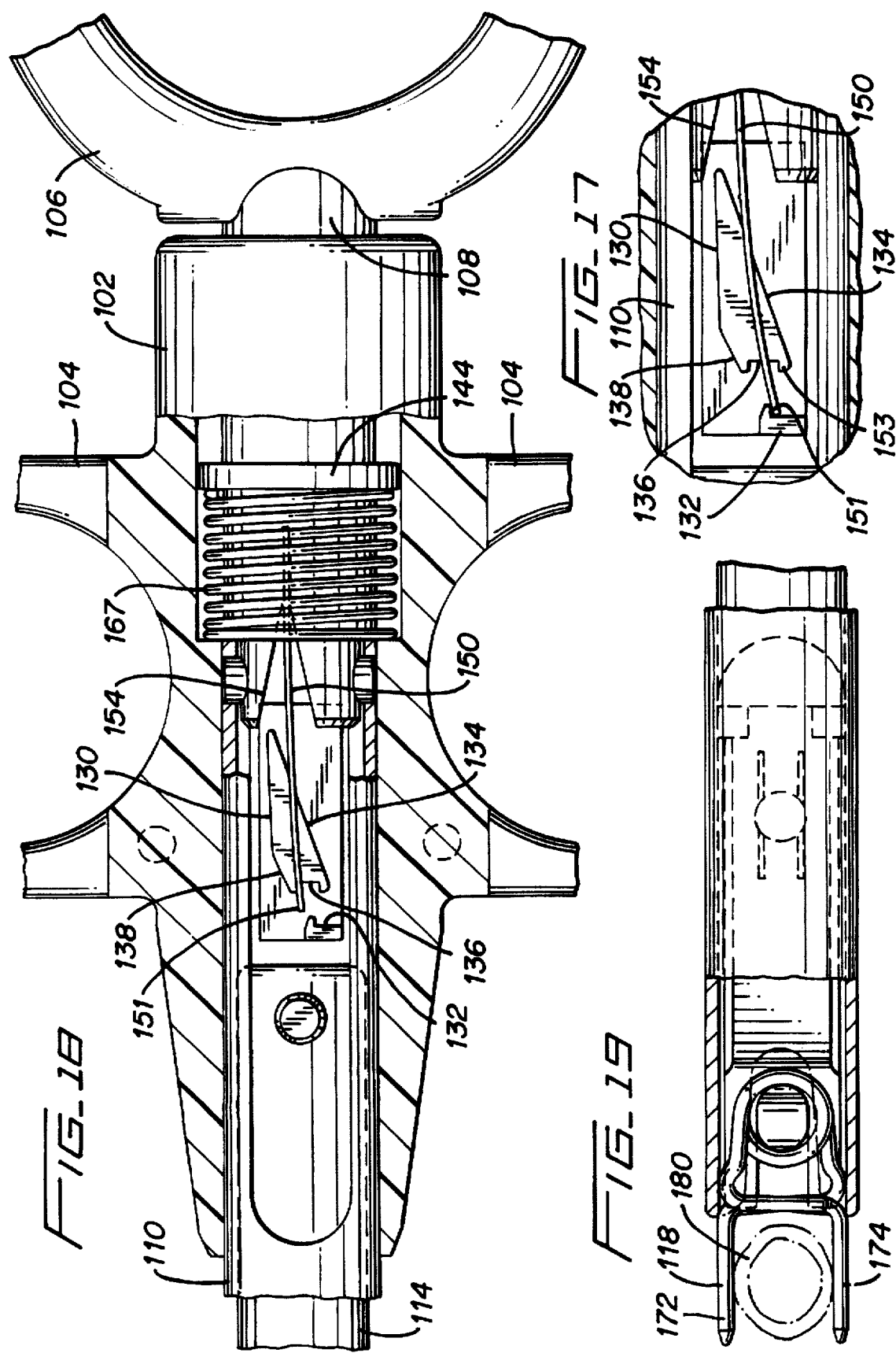

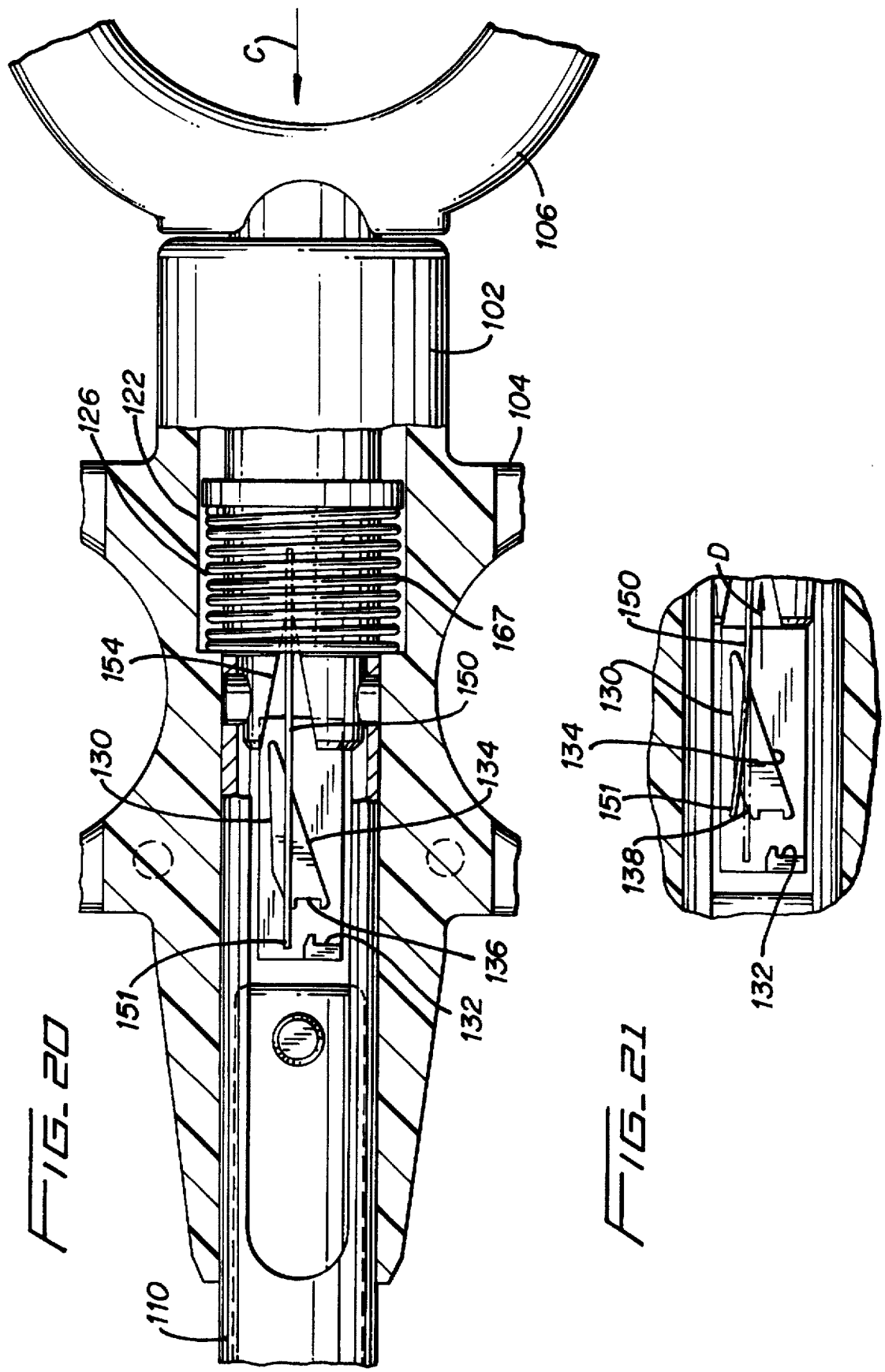

CLAMP APPLICATOR

BACKGROUND

1. Technical Field

The present disclosure relates generally to surgical clamps and to surgical instruments for applying surgical clamps. More specifically, the present disclosure relates to a vascular spring clamp and to a spring clamp applicator for applying the spring clamp to a patient's vasculature during a surgical procedure.

2. Background of Related Art

Vascular spring clamps are well known. Typically, these clamps are used in procedures to clamp vessels to prevent excessive blood loss and to maintain a reasonably clear operating field. The clamps are extremely small in size, generally having a length of no more than approximately ten millimeters, and require precise placement to achieve their intended purpose.

One such clamp is the Yacoubian clamp which includes a pair of legs having sharpened tips interconnected to a pair of arms by a spring coil. The sharpened tips are configured to penetrate the soft fatty tissue surrounding a blood vessel. Upon closure of the clamp, the vessel is occluded by the clamp legs which are cushioned by the fatty tissue. Although the Yacoubian clamp provides effective occlusion of a blood vessel, it is bulky in size and subjects the blood vessel to risk of penetration by the sharpened tips.

Instruments for applying vascular spring clamps to blood vessels are also well known. For example, U.S. Pat. No. 3,518,993 ("Blake") discloses an instrument which includes a pair of jaws which support a clamp and a cylindrical barrel. A lever is actuable to open the clamp so that it may be applied to a blood vessel. Actuation of the lever causes movement of the clamp with respect to the blood vessel to be clamped, thus making precise placement of the clamp about the blood vessel very difficult.

U.S. Pat. Nos. 5,304,183 ("Gourlay") and 4,367,746 ("Derechinsky") also disclose clamp applicators. Gourlay's instrument includes a linearly movable actuator including a plunger which is movable to move a clamp from an open position to a closed position. Derechinsky's instrument includes a pistol-type grip having a lever which is movable to move the clamp from an open to a closed position. Both Gourlay's and Derechinsky's clamp applicators require prolonged movement of an actuator against the bias of a biasing means to initiate placement of a clamp about a blood vessel. Such movement compromises the accuracy of clamp placement.

Accordingly, a need exists for an improved clamp applicator which overcomes the above-noted disadvantages, is easy to use and manufacture, and is capable of accurately placing clamps about body tissue. A need also exists for a spring clamp that is relatively small in size, easy to apply and remove, and does not risk penetration of the blood vessel being clamped.

SUMMARY

A clamp applicator for applying a resilient clamp to vasculature are provided. The applicator includes a housing and an elongated clamp support member which extends distally from and is fixedly positioned with respect to the housing. A clamp support post is positioned at the distal end of the support member and is configured to receive a clamp thereon. An actuator extends from one end of the housing. The actuator is connected to a tubular actuation member which is movable about the clamp support member from a retracted to an advanced position. The tubular actuation member includes an annular camming surface which is movable into engagement with camming arms of the resilient clamp to bias a pair of jaws or legs of the clamp from an open to a closed position. The clamp legs preferably include blunt tips which are configured to penetrate soft fatty tissue but not to present a risk of penetration of a blood vessel. The applicator also includes a locking device for retaining the tubular actuation member in the advanced position to facilitate positioning of the clamp about body tissue. Limited movement of the actuator is required to move the applicator from the locked position to the retracted position. This limited movement prevents inaccurate placement of the clamp about body tissue caused by prolonged movement of the actuator during actuation of the applicator.

In a preferred embodiment, the locking device includes a retaining member having a base portion fixed to the housing and a resilient proximal portion having a locking member. The locking member is movable into engagement with the actuator to retain the tubular actuation sleeve in the advanced position. The resilient proximal portion can be easily deflected downwardly with a limited amount of movement to release the actuator. Alternately, the locking device may include a camming plate fixed within the housing and a flexible locking member movable in conjunction with the actuator into engagement with the camming plate to retain the actuator and tubular actuating sleeve in the advanced position. The locking device is moved to a locked position by moving the actuator a first distance in the distal direction and may be released by moving the actuator a second distance substantially less than the first distance in the distal direction.

BRIEF DESCRIPTION OF THE DRAWINGS

Various preferred embodiments are described herein with reference to the drawings, wherein:

FIG. 3 is a side cross-sectional view of the proximal end of the clamp applicator shown in FIG. 1 in the retracted position;

FIG. 3A is a cross-sectional view taken along section line 3A—3A of FIG. 3;

FIG. 4 is a side cross-sectional view of the distal end of the clamp applicator shown supporting a clamp and illustrating the sleeve in the retracted position;

FIG. 5 is a side cross-sectional view of the proximal end of the clamp applicator shown in FIG. 1 in the advanced position;

FIG. 6 is a side cross-sectional view of the distal end of the clamp applicator shown supporting a clamp and illustrating the sleeve in an advanced position;

FIG. 7 is a perspective view of an alternate embodiment of the clamp applicator shown supporting a clamp;

FIG. 8 is an enlarged perspective view of the distal end of the clamp applicator and clamp shown in FIG. 7;

FIG. 9 is a perspective view with parts separated of the clamp applicator and clamp shown in FIG. 7;

FIG. 9A is an enlarged plan view of the retaining member of the clamp applicator shown in FIG. 9;

FIG. 10 is a side cross-sectional view of a portion of the proximal end of the clamp applicator shown in FIG. 7 in the retracted position;

FIG. 11 is a side cross-sectional view of the distal end of the clamp applicator and clamp of FIG. 7 shown in the retracted position;

FIG. 12 is a top partial cross-sectional view of the distal end of the clamp applicator and the clamp shown in FIG. 7;

FIG. 12A is a top enlarged view of the clamp of FIG. 7;

FIG. 13 is a top partial cross-sectional view of the proximal end of the clamp applicator of FIG. 7 shown in the retracted position;

FIG. 14 is a top cross-sectional view of the distal end of the clamp applicator and clamp of FIG. 7 shown in the retracted position;

FIG. 15 is a top partial cross-sectional view of the proximal end of the clamp applicator of FIG. 7 shown in a partially advanced position;

FIG. 16 is a top cross-sectional view of the distal end of the clamp applicator and clamp of FIG. 7 shown in a partially advanced position with the clamp partially opened;

FIG. 17 is a top enlarged view of the locking mechanism of the clamp applicator of FIG. 7 shown in the fully advanced position;

FIG. 18 is a top partial cross-sectional view of the proximal end of the clamp applicator of FIG. 7 shown in the locked position;

FIG. 19 is a top cross-sectional view of the distal end of the clamp applicator of FIG. 7 shown in the locked position with the clamp fully opened;

FIG. 20 is a top cross-sectional view of the proximal end of the clamp applicator of FIG. 7 shown in a fully advanced position;

FIG. 21 is a top enlarged view of the locking mechanism of the clamp actuator in a release position;

DETAILED DESCRIPTION OF THE PREFERRED EMBODIMENTS

Figure 1:
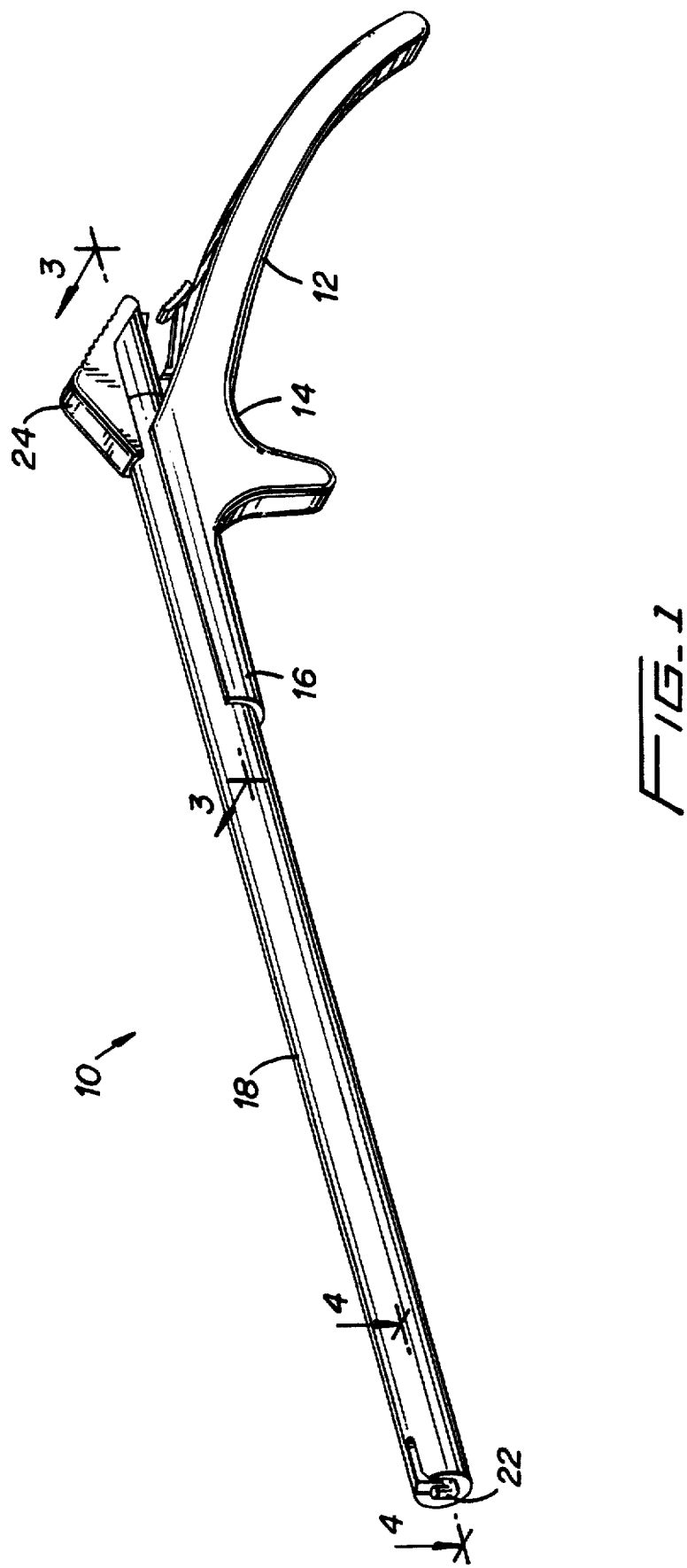
FIG. 1 is a perspective view of one embodiment of the clamp applicator.

Preferred embodiments of the presently disclosed clamp applicator will now be described with reference to the drawings, in which like reference numerals designate identical or corresponding elements in each of the several views.

Figure 2:
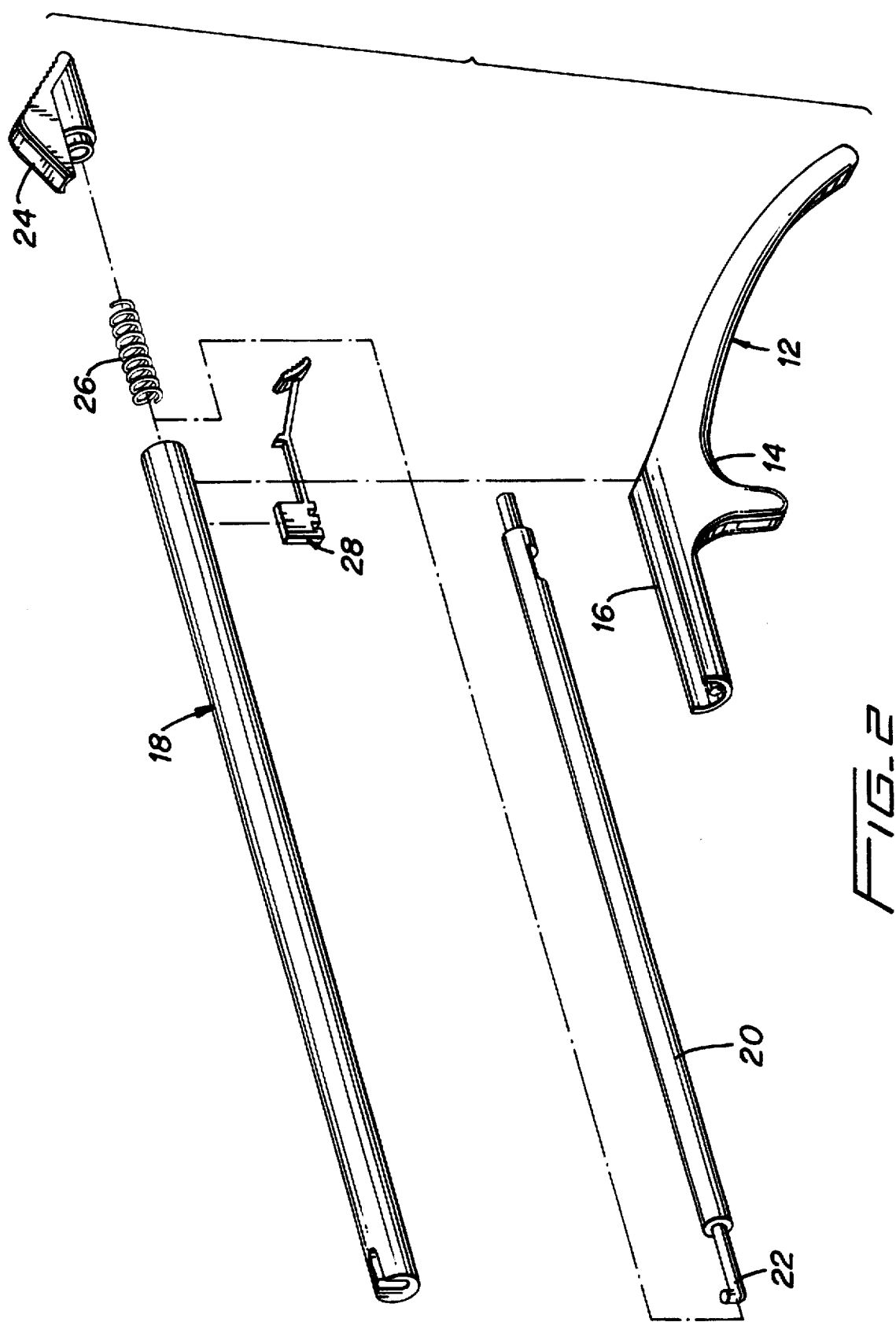
FIG. 2 is a perspective view with parts separated of the clamp applicator shown in FIG. 1.

One embodiment of the presently disclosed clamp applicator will now be described with reference to FIGS. 1–6. FIGS. 1 and 2 illustrate the clamp applicator shown generally as 10. Briefly, clamp applicator 10 includes a handle member 12 having a gripping portion 14 and a semi-cylindrical track portion 16. A tubular actuating sleeve 18 dimensioned to be slidably supported within the track portion 16 extends distally from the handle member 12. An elongated rod 20 is positioned within the actuating sleeve 18 and is provided with a distal hook portion 22 for engaging a clamp. An actuating member 24 is secured to the proximal end of the actuating sleeve 18 to advance the sleeve 18 distally against the bias of a biasing member 26. A locking device including retaining member 28 is secured adjacent to the handle member 12 and functions to retain the actuating sleeve 18 in a distal position.

Referring to FIGS. 3 and 4, the actuating sleeve 18 is linearly slidably along the track portion 16 of handle member 12. The track portion 16 is provided with a substantially T-shaped projection 30 which is configured to be received in a correspondingly shaped groove 32 formed in the actuating sleeve 18. The groove 32 has a longitudinal length greater than that of the projection 30 to facilitate longitudinal movement of the actuating sleeve 18 with respect to track portion 16, while preventing the actuating sleeve 18 from becoming disengaged from handle member 12. Alternatively, any known interlocking structure which permits relative linear movement between sleeve 18 and handle member 12 may be substituted for projection 30 and groove 32.

The retaining member 28 includes a base portion 34 and a proximally extending resilient portion 36. The base portion 34 has a bottom surface 38 which is fixedly secured to the handle member 12 and a top surface 40 which is fixedly received within a slot 42 provided in the proximal end of the elongated rod 20. Engagement between top surface 40 and slot 42 fixedly secures the rod 20 with respect to handle member 12 within actuating sleeve 18. The actuating member 24 is provided with a blind bore 46. The biasing member 26, which is preferably a coil spring, is positioned between the proximal end 44 of the elongated rod 20 and blind bore 46 to urge the actuating sleeve 18 proximally.

The actuation member 24 may be secured to or formed integrally with the actuating sleeve 18 and preferably includes a knurled or grooved proximal surface 48 to facilitate gripping. A locking surface 50 and a cam surface 52 are provided on a bottom portion of the actuation member. The locking surface 50 and cam surface 52 are positioned to engage a locking member 53 located at the proximal end of resilient portion 36 of retaining member 28 to retain the tubular sleeve 18 in an advanced position. A thumb engagement member 54 also located on the proximal end of retainer member 28 may be acted upon to disengage locking surface 50 and locking member 53.

Operation of the clamp applicator 10 will now be described with reference to FIGS. 3–6. FIGS. 3 and 4 illustrate clip applicator 10 in a retracted position in which biasing member 26 has urged actuating member 24 and actuating sleeve 18 to their proximal-most positions. In the retracted position, the distal end of hook portion 22 extends from the distal end of actuating sleeve 18, thus permitting a clamp 60 to be supported on the hook 22.

Referring now to FIGS. 5 and 6, an external force may be applied by, for example, a surgeon on actuating member 24 in the direction indicated by arrow "A" in FIG. 5, to move the actuating member 24 and actuating sleeve 18 distally as indicated by arrow "B" in FIG. 6 to an advanced position in which the distal end 25 of actuating sleeve 18 engages a pair of cam surfaces 62 on clamp 60 to force legs or jaws 60a and 60b of clamp 60 to an open position. That is, as cam surfaces 62 are forced toward each other, the legs or jaws 60a and 60b are spread apart. Legs 60a, 60b have blunt tips configured to penetrate soft tissue about a vessel. As actuating member 24 is moved to the advanced position, cam surface 52 of actuating member 24 engages and deflects resilient portion 36 of retainer member 28 downwardly. When locking surface 50 is moved to avocation distal of locking member 53, locking member 53 returns to an undeflected position into engagement with locking surface 50 to retain the actuating sleeve in the advanced position and thus retain clamp 60 in the open position. That is, locking member 53 prevents proximal movement of actuating member 24. The clamp 60 may now be positioned about body tissue 66 to be clamped. To return the actuation sleeve 18 proximally to close clamp 60 about body tissue 66, engagement member 54 is pressed downwardly, as viewed in FIG. 5, to move locking member 53 from engagement with locking surface 50 and allow biasing member 26 to move actuation member 24 proximally. Proximal movement of actuating member 24 retracts actuating sleeve 18 to disengage the distal end of actuating sleeve 18 from cam surfaces 62 to enable legs 60a and 60b of clamp 60 to return to their normally closed position. To remove the clamp, e.g. at the end of the procedure, clamp applicator 10 is reinserted to the surgical site and hook portion 22 is placed into engagement with the clamp 60, actuating sleeve 18 is moved distally to open the legs 60a, 60b to remove clamp 60 from the tissue, and the applicator 10 and clamp 60 are removed from the body.

A further embodiment of the presently disclosed clamp applicator will now be described with reference to FIGS. 7-23. FIGS. 7 and 8 illustrate the clamp applicator shown generally as 100. Briefly, clamp applicator 100 includes a housing 102 having a pair of diametrically opposed finger loops 104. An actuator 106 extending from the proximal end of the housing has a cylindrical body portion 108 slidably disposed within the housing 102. A tubular actuating member or sleeve 110 having an annular camming surface 112 at its distal end extends from the housing 102. A clamp support member 114 extends from the distal end of the actuating member and includes a support post 116 about which a clamp 118 may be positioned. A resilient release member 120 is supported adjacent to the distal end of the support member 114 to assist in releasing clamp 118 from the support post 116.

Referring now to FIGS. 9-10, housing 102 is preferably formed from molded housing half-sections 102A and 102B. The half-sections define a stepped longitudinal bore 122 having a forward portion 124 and a rear portion 126. A locking device 128 is preferably integrally molded with housing half-section 102B within the forward portion 124 of longitudinal bore 122. Alternately, locking device 128 may be formed separately from housing half-section 102B and attached within longitudinal bore 122 using any known fastening device, such as, for example, an adhesive. The locking device 128 includes a camming plate 130 and a retaining member 132. A post 140 extending between the housing half-sections is configured to extend through an opening 142 formed in the proximal end of the clamp support member 114 to secure the support member with respect to the housing 102.

The cylindrical body portion 108 of actuator 106 is provided with an annular ring 144 which is slidably positioned within the rear portion 126 of longitudinal bore 122. The distal end of cylindrical body portion 108 includes diametrically opposed ears 146 and a fastening groove 148 for securing a flexible locking member 150. Ears 146 are positioned within openings 152 formed in the proximal end of actuating member or sleeve 110 such that movement of actuator 106 causes corresponding movement of actuating member 110. The fastening groove 148 includes a V-shaped portion 154 and a toothed portion 156. (See FIGS. 13 and 15). The proximal end of locking member 150 is frictionally secured within toothed portion 156 such that the central portion of locking member 150 is free to bend within V-shaped portion 154.

Referring also to FIGS. 11 and 12, the distal end of clamp support member 114 includes a securement post 158 dimensioned to be received within an opening 160 provided in the proximal end of the resilient member 120. The securement post 158 is located proximally of clamp support post 116, such that fingers 162 of resilient release member 120 are positioned on both sides of support post 116 to assist clamp 118 in being released from the support post 116. The proximal end of clamp support member 114 extends through actuation member 110 and includes opening 142 which is fixedly secured about housing post 140 to secure the support member 114 with respect to housing 102. A biasing spring 167 positioned within rear portion 126 of stepped bore 122 between annular ring 144 and bore wall 164 urges the actuation member 110 proximally with respect to the clamp support member 114.

Referring to FIG. 12A, clamp 118 is constructed from a single length of shape memory material such as, for example, spring wire. The clamp 118 includes a spring section having a coil 166 and first and second camming arms 168 and 170, and a clamping section having first and second jaws or legs 172 and 174. Each leg includes a blunt tip 172a and 174a configured to penetrate soft fatty tissue 175 located about a vessel 177. The coil 166 is dimensioned to be fitted about the support post 116 (See FIG. 12). To open the clamp 118, first and second camming arms 168 and 170 are pressed towards each other to flex the shape memory material and move jaws or legs 172 and 174 away from each other. Preferably, the clamp has an overall length L ranging from about 0.2 inches to about 1 inch and more preferably about 0.5 inches.

Referring now to FIGS. 13-23 operation of the clamp applicator will now be described in detail. As illustrated in FIGS. 13 and 14, actuator 106 is biased by spring 162 proximally, thus moving tubular actuation member 110 to a retracted position in which annular camming surface 112 is spaced from clamp 118. Clamp 118 is positioned about support post 116 above fingers 162 of resilient release member 120 by sliding coil 166 of clamp 118 onto the support post 116.

Referring to FIGS. 15 and 16, actuator 106 is moved distally against the bias of spring 167 in the direction indicated by arrow "A" in FIG. 15 a first distance to advance the tubular actuation member 110 in the direction indicated by arrow "B" in FIG. 16 into engagement with clamp 118. Annular camming surface 112 engages first and second camming arms 168 and 170 to press the legs towards each other to partially open the jaws 172 and 174. Engagement between camming arms 168 and 170 and camming surface 112 of tubular actuating sleeve 110 retains clamp 118 on support post 116 above release member 120. Locking member 150 is also advanced distally to move base portion 151 of locking member 150 into engagement with first cam surface 134 of camming plate 130 such that locking member 150 is deflected outwardly.

As illustrated in FIG. 17, when the actuator is advanced to a position in which base portion 151 passes over the edge 153 of camming plate 130, the flexible locking member 150 attempts to return to its linear configuration, but is prevented from doing so by retaining member 132. Retaining member 132 catches and retains base portion 151 at a position aligned with retention slot 136.

Referring now to FIGS. 18 and 19, when the actuator 106 is released to allow biasing spring 167 to move the actuator and thus tubular actuation member 110 proximally, base portion 151 of locking member 150 is trapped within retention slot 136 to is lock the actuator 106 and actuator member 110 in the distal position. In the distal position, the clamp 118 is held open and may be easily positioned about body tissue 180 to be clamped.

Referring to FIGS. 20 and 21, after the jaws 172 and 174 are properly positioned about tissue 180 (FIG. 19), actuator 106 is again advanced distally a second distance, which is substantially shorter than the first distance, in the direction indicated by arrow "C", to move base portion 151 of locking member 150 from retention slot 136. The second distance of advancement must be at least equal to the depth of the retention slot 136. Upon being moved from the retention slot 136, the locking member 150 returns to its linear configuration, which is no longer aligned with retention slot 136. Upon release of actuator 106, biasing spring 167 returns the actuator 106 and actuation member 110 proximally to the retracted position previously shown in FIGS. 13 and 14 to allow jaws or legs 172 and 174 to close about tissue 180. Because locking member 150 is no longer aligned with retention slot 136, base portion 151 is free to move along second camming surface 138 as indicated by arrow "D" in FIG. 21 around the camming plate 130 to its original position (FIG. 13). In the retracted position of tubular actuation member 110, in which camming arms 168 and 170 of clamp 118 no longer engage camming surface 112, resilient release member 120 urges clamp 118 upwardly off of support post 116.

Figure 22:
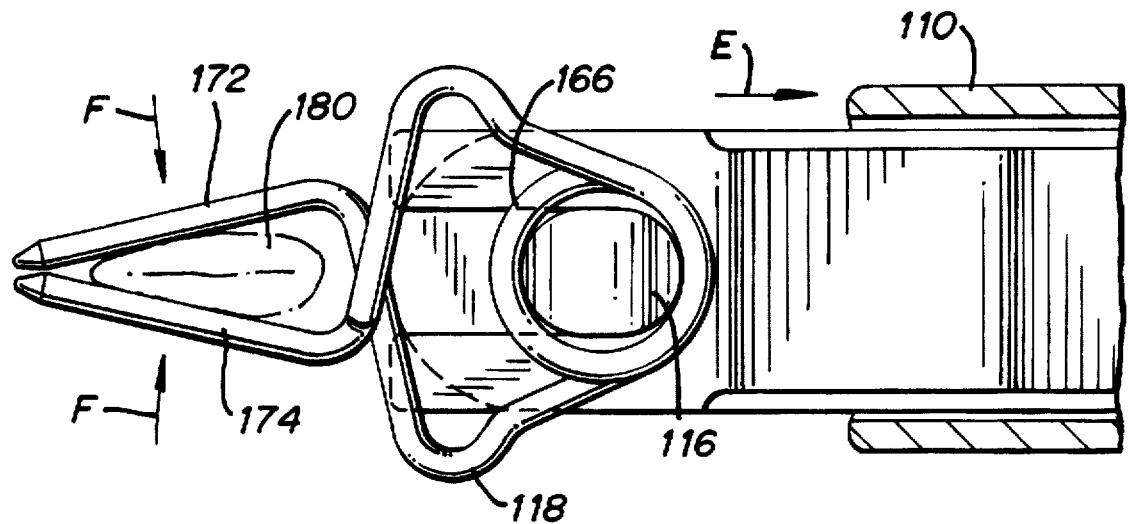
FIG. 22 is a top cross-sectional view of the distal end of the clamp actuator and clamp of FIG. 7 shown in the retracted position with the clamp closed about body tissue.
Figure 23:
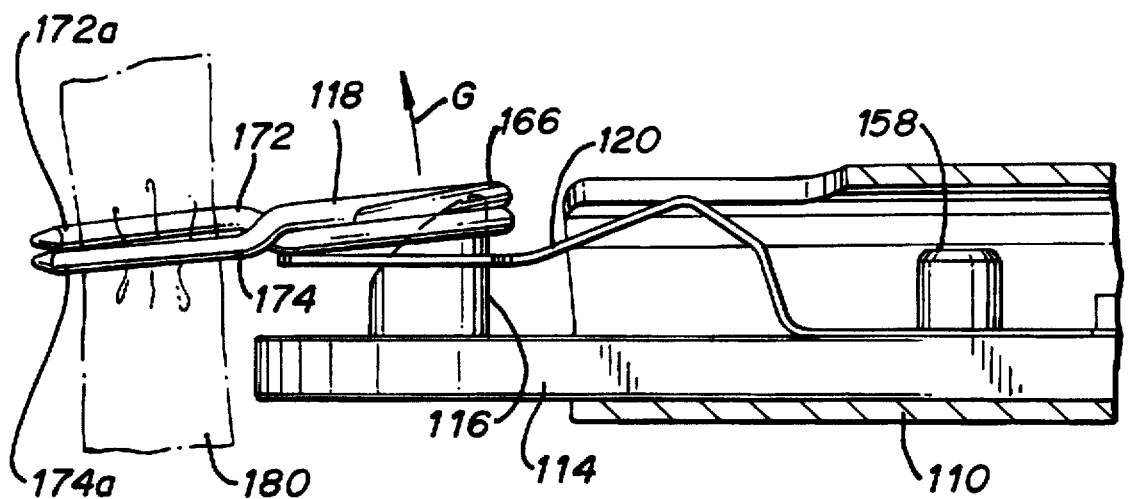
FIG. 23 is a side cross-sectional view of the distal end of the clamp actuator and clamp of FIG. 7 during removal of the clamp from the clamp support post.

Referring to FIGS. 22 and 23, as actuation member 110 returns to the retracted position as indicated by arrow "E" in FIG. 22, jaws or legs 172 and 174 of clamp 118 close about tissue 180 in the direction indicated by arrows "F". Clamp 118 is removed from clip applicator 100 by the urging of resilient release member 120 and by poring the applicator 100 downwardly to slide coil 166 from post 116. To retrieve the clamp 118 from tissue, e.g. at the end of the procedure, applicator 100 is reintroduced to the surgical site and positioned such that support post 116 engages coil 166 of clamp 18. Actuating member 110 is moved distally in the manner described above to open jaws 182, 174 to release the clamp 118 from the tissue to withdraw it with the applicator 100 from the body.

Figure 24:
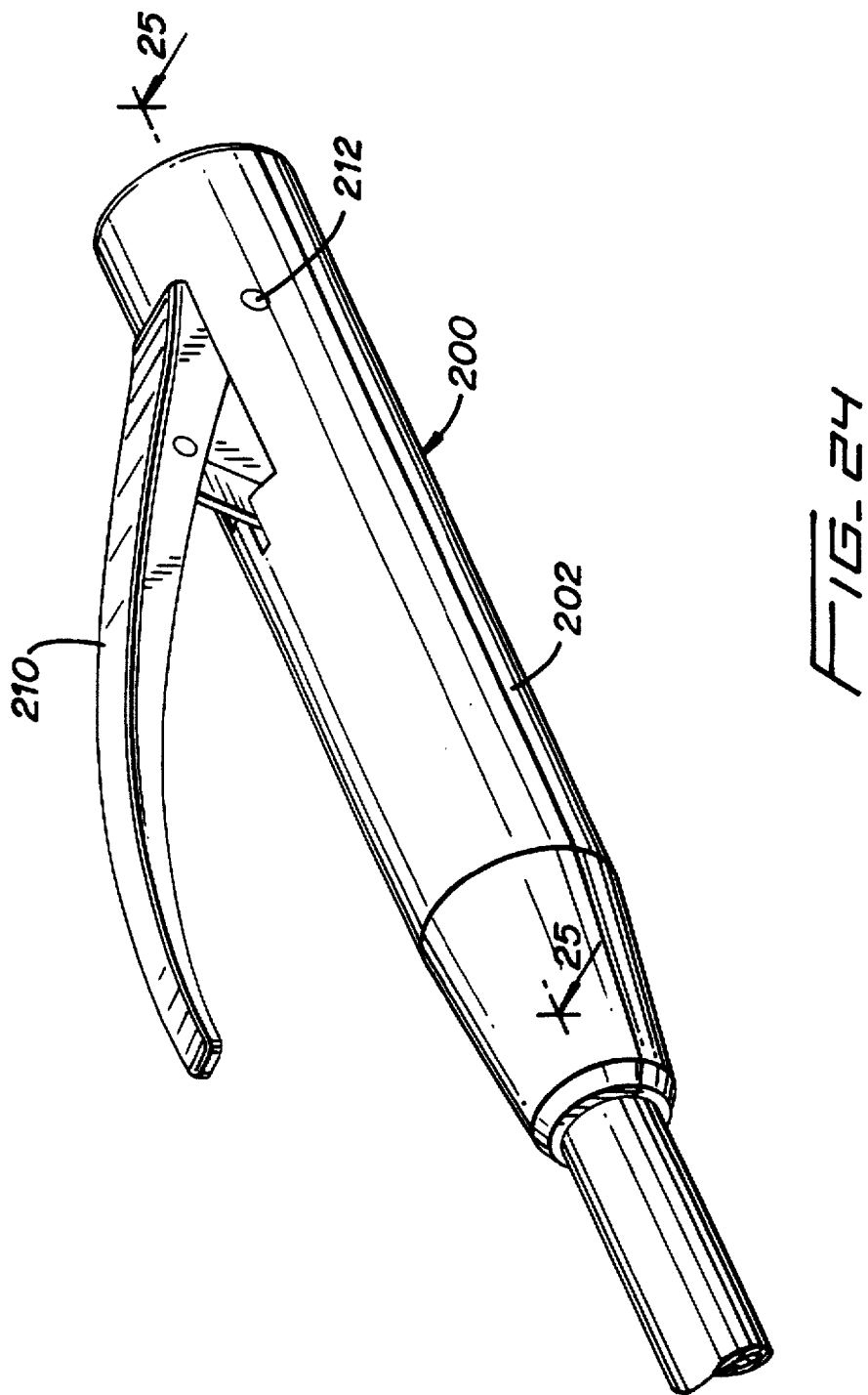
FIG. 24 is a perspective view of the proximal end of another alternate embodiment of the clamp applicator.
Figure 25:
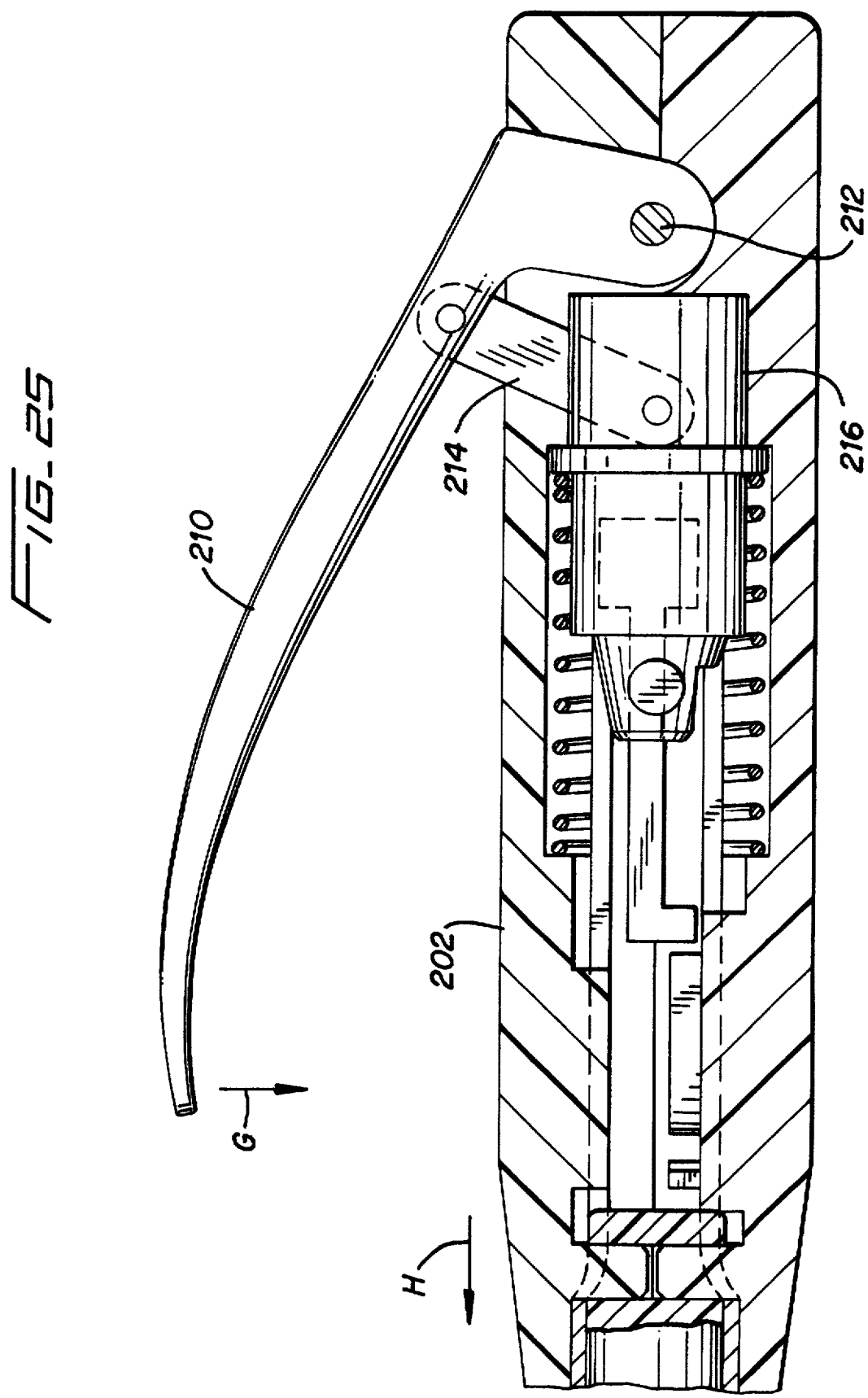
FIG. 25 is a cross-sectional view taken along section line 25—25 of FIG. 24.

An alternate embodiment of the clamp applicator is illustrated in FIGS. 24 and 25. In this embodiment, the clamp applicator, shown generally as 200, includes a lever type actuator. A lever 210 is pivotably mounted to housing 202 about pivot pin 212. A link 214 is pivotably connected to lever 210 at one end and to cylindrical portion 216 at the other end. When lever 210 is pivoted towards housing 202 as indicated by arrow "G" in FIG. 25, tubular actuation member 218 is advanced distally, as indicated by arrow "H".

Figure 26:
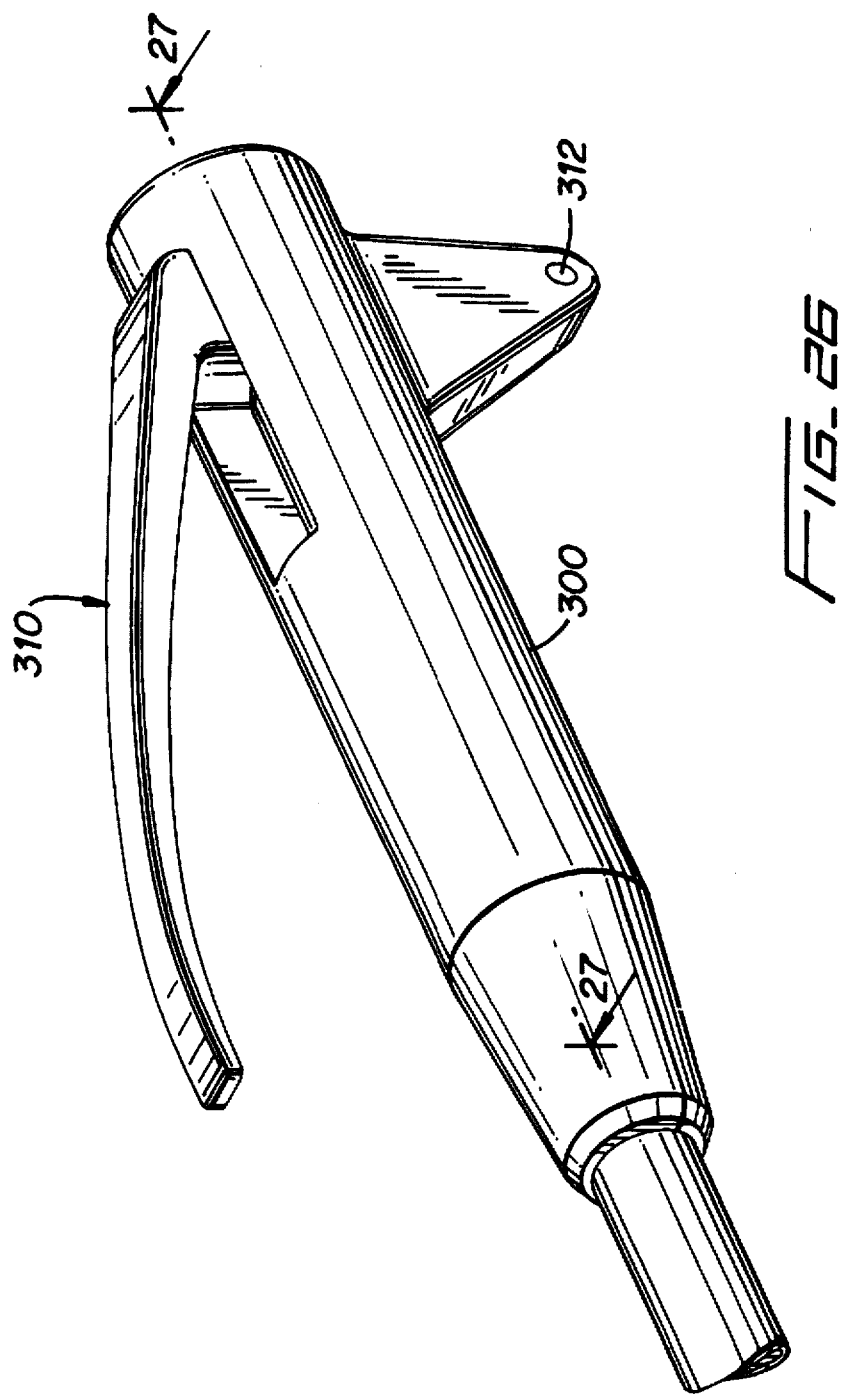
FIG. 26 is a perspective view of the proximal end of still another alternate embodiment of the clamp applicator.
Figure 27:
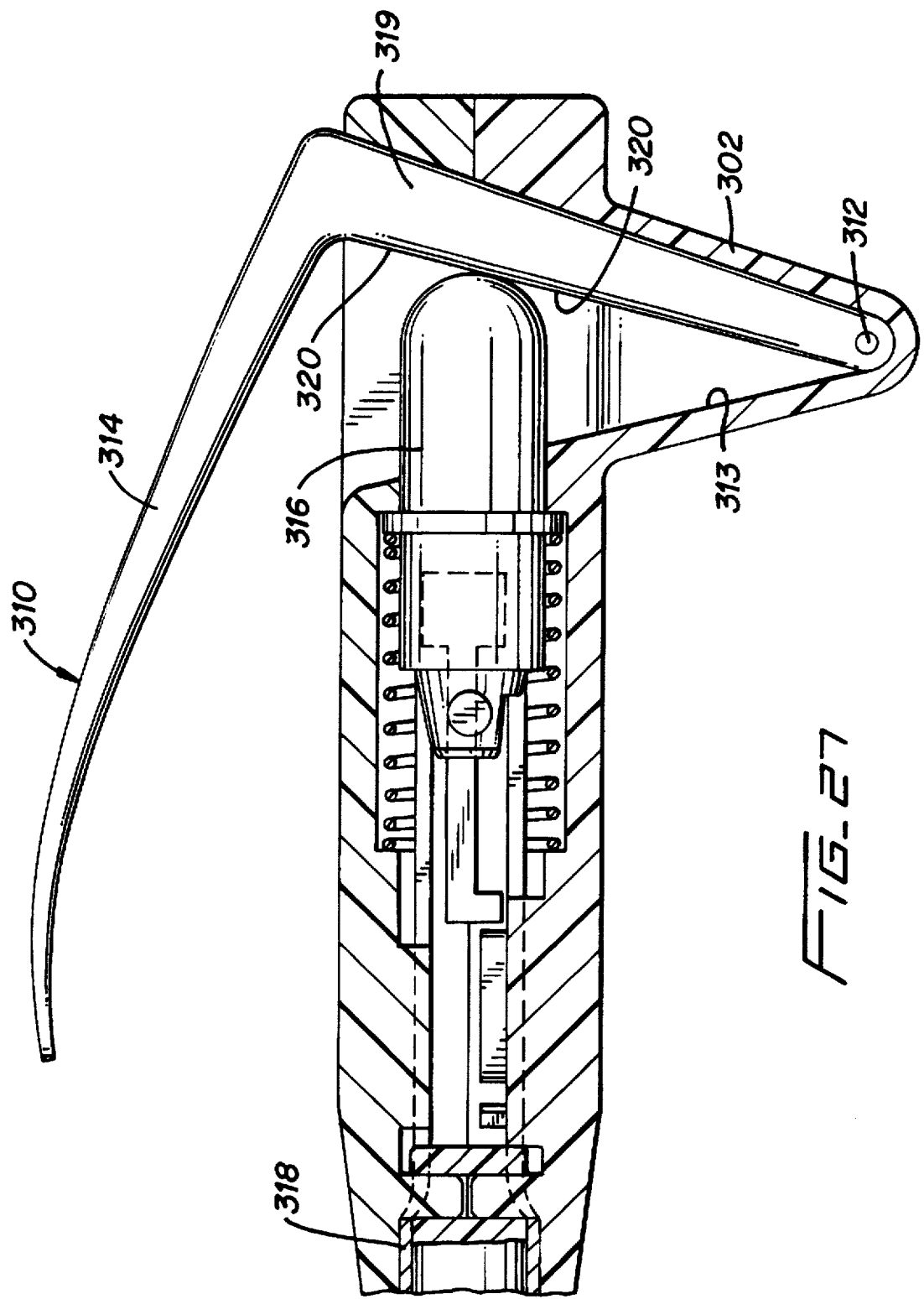
FIG. 27 is a cross-sectional view taken along section line 27—27 of FIG. 26.

Another alternate embodiment of the clamp applicator is illustrated in FIGS. 26 and 27. In this embodiment, the clamp applicator, shown generally as 300, also includes a lever type actuator. A lever 310 is pivotably mounted to housing 302 about a pivot pin 312 within a recess 313 formed in housing 302. The lever 310 includes a handle portion 314 and an angled portion 319. The angled portion 319 includes an abutment surface 320 which engages and advances cylindrical portion 316 distally within the housing 302 as lever 310 is pivoted about pivot member 312 in a counter-clockwise direction. Advancement of cylindrical portion 316 causes corresponding advancement of tubular actuation member 318.

The clamp applicator and low profile clamp are suitable for use in many different surgical procedures. Referring to FIG. 12A, one example of use of the clamp is during a coronary bypass procedure, wherein the left anterior descending coronary artery is clamped above and below the anastomosis site. The blunt tips 172a and 174a of the clamp 118 are able to penetrate the fatty tissue 175 surrounding the coronary artery 177 and gently occlude the coronary artery by pressing against the surrounding tissue which in turn presses against the vessel. Because the tips are blunt, the danger of the tips penetrating the coronary artery is minimized.

Another example of use of the clamp is to clamp tissue about the interior mammary artery for temporary occlusion (clamping). The clamp can also and serve as a marking device by placing a string through the loop on the clamp to locate the end of the vessel.

The clamp is suitable for the foregoing procedure because it is can be easily placed and easily removed from the artery as described above. It is also suitable because of its relatively low profile which prevents the clamp from blocking access to the anastomotic site or otherwise interfering with the procedure.

It will be understood that various modifications may be made to the embodiments disclosed herein. For example, the actuator may be biased to the advanced position rather than to the retracted position as shown. Also, a soft foam tube can be placed on the ends of the legs of the clamp so that vessels can be clamped directly with reduced trauma. Therefore, the above description should not be construed as limiting, but merely as exemplifications of preferred embodiments. Those skilled in the art will envision other modifications within the scope and spirit of the claims appended thereto.

What is claimed is:

1. A clamp applicator for applying a resilient clamp having a normally closed position to body tissue, the clamp applicator comprising:

a) a housing;
   b) a clamp support member positioned distally of the housing and configured to support a resilient clamp;
   c) an actuator positioned around the clamp support member and being movably mounted in relation to the clamp support member, a biasing member operably associated with the actuator, wherein the actuator is configured to urge the resilient clamp from the normally closed position to an open position; and
   d) a locking device operably associated with the actuator, the locking device being positioned to retain the actuator and clamp support member at relative positions to maintain a resilient clamp in the open position.

2. A clamp applicator according to claim 1, wherein the actuator is movable in relation to the clamp support member between a retracted position in which a resilient clamp is in the normally closed position and an advanced position in which a resilient clamp is in the open position.

3. A clamp applicator according to claim 1, wherein the clamp support member is fixed with respect to the housing, and the actuator is movable with respect to the housing and the clamp support member from a first position in which the resilient clamp is in the normally closed position to a second position in which a resilient clamp is biased to the open position.

4. A clamp applicator according to claim 3, wherein the actuator includes a tubular sleeve having a distal end, the tubular sleeve being linearly movable with respect to the clamp support member to move the distal end of the tubular sleeve into engagement with a resilient clamp to bias the resilient clamp from the normally closed position to the open position.

5. A clamp applicator according to claim 3, wherein the locking device includes a flexible retaining member having a base portion fixed to the housing and a locking member movable into operative engagement with the actuator to retain the actuator in the second position.

6. A clamp applicator according to claim 5, wherein the actuator includes a locking surface and a cam surface, wherein the locking member of the flexible retaining member is deflected along the cam surface as the actuator is moved from the first position to the second position, the locking member returning to an undeflected position into engagement with the locking surface of the actuator after passing over the cam surface.

7. A clamp applicator according to claim 6, wherein the retaining member has an engagement portion, the engagement portion being movable to move the locking member from engagement with the locking surface of the actuator, thus permitting is the biasing member to return the actuator to the first position to allow a resilient clamp to return to the normally closed position.

8. A clamp applicator for applying a resilient clamp having a normally closed position to body tissue, the clamp applicator comprising:

a) a housing;

b) a clamp support positioned distally of the housing and configured to support a resilient clamp;

c) an actuator movably mounted in relation to the clamp support member, a biasing member operably associated with the actuator, the actuator being configured to urge the resilient clamp from the normally closed position to an open position; and d) a locking device operably associated with the actuator, the locking device being positioned to retain the actuator and clamp support member at relative positions to maintain a resilient clamp in the open position wherein the clamp support member is fixed with rest to the housing, and the actuator is movable with respect to the housing and the clamp support member from a first position in which the resilient clamp is in the normally closed position to a second position in which a resilient clamp is biased to the open position, and wherein the locking device includes a camming plate and a flexible locking member, the flexible locking member being movable into operative engagement with the camming plate to retain the actuator in the second position.

9. A clamp actuator according to claim 8, wherein the camming plate includes a first cam surface and a retention slot, the flexible locking member being movable into engagement with the first cam surface as the actuator is moved from the first position to the second position to bend the flexible locking member such that when the flexible locking member moves past the cam surface, the flexible locking member elastically moves into engagement with the retention slot.

10. A clamp applicator according to claim 9, wherein the locking device further includes a retaining member, the retaining member being positioned on the camming plate to direct the flexible locking member into the retention slot.

11. A clamp applicator according to claim 10, wherein the actuator includes a tubular actuation sleeve having a distal camming surface, the distal camming surface being movable into engagement with a resilient clamp to bias the resilient clamp from the normally closed position to the open position.

12. A clamp applicator according to claim 11, wherein the clamp support member includes a distally extending rod, the distally extending rod being positioned within the actuation sleeve and having a proximal end fixedly secured to the housing.

13. A clamp applicator according to claim 12, further including a resilient release member secured to the distal end of the distally extending rod, the resilient release member being positioned to assist in releasing a resilient clamp from the clamp support member clamp support post.

14. A clamp applicator for applying a resilient clamp having a normally closed position to body tissue, the clamp applicator comprising:

a) a housing;

b) a clamp support member extending distally from the housing and having a longitudinal axis, the clamp support member configured to support a resilient clamp;

c) an actuator movable relative to the clamp support member to bias the resilient clamp from the normally closed position to an open position; and d) a locking device operably associated with the actuator, the locking device being movable to a locked position in which a resilient clamp is maintained in the open position;

wherein the actuator is movable in a first direction a first distance to move the locking device to the locked position and the actuator is movable in the first direction a second distance substantially shorter than the first distance to release the actuator and permit a resilient clamp to return to the normally closed position.

15. A clamp applicator according to claim 14, wherein the locking device includes a camming plate and a flexible locking member, the flexible locking member being movable over the first distance into the locked position in which the flexible locking member is in operative engagement with the camming plate.

16. A clamp applicator according to claim 15, wherein the camming plate includes a first cam surface and a retention slot, the flexible locking member being movable into engagement with the first cam surface as the actuator is moved over the first distance to bend the flexible locking member such that when the flexible locking member passes off the cam surface, the flexible locking member elastically moves into engagement with the retention slot.

17. A clamp applicator according to claim 16, further including a biasing member, the biasing member being operatively associated with the actuator to urge the actuator to a position to allow a resilient clamp to remain in an open position.

18. A clamp applicator according to claim 17, wherein the locking device further includes a retaining member, the retaining member being positioned on the camming plate to direct the flexible locking member into the retention slot.

* * * * *